United States Patent [19]

McCullough, Jr. et al.

[11] Patent Number: 5,264,137

[45] Date of Patent: Nov. 23, 1993

[54] METHOD FOR SEPARATING FLUIDS USING A CARBONACEOUS POLYMERIC FILTER HAVING A LOI GREATER THAN 40

[75] Inventors: Francis P. McCullough, Jr., Lake Jackson; Stuart D. Stein, Freeport, both of Tex.

[73] Assignee: The Dow Chemical Company, Midland, Mich.

[21] Appl. No.: 894,899

[22] Filed: Jun. 8, 1992

Related U.S. Application Data

[62] Division of Ser. No. 581,339, Sep. 11, 1990, Pat. No. 5,151,198.

[51] Int. Cl.$^5$ .............................................. B01D 39/06
[52] U.S. Cl. ................................... 210/767; 210/243; 210/315; 210/489; 210/503; 95/273
[58] Field of Search ............... 210/188, 243, 314, 315, 210/488, 489, 492, 496, 497.2, 503, 508, 767, DIG. 5, DIG. 6; 55/97, 185, 186, 187, 487, 489, DIG. 17, DIG. 25; 428/284, 285, 368, 369

[56] References Cited

U.S. PATENT DOCUMENTS

| | | | |
|---|---|---|---|
| 4,604,205 | 8/1986 | Ayers | 210/508 |
| 4,948,515 | 8/1990 | Okumura et al. | 210/243 |
| 4,999,108 | 3/1991 | Kach et al. | 210/243 |
| 5,007,994 | 4/1991 | Snee | 210/243 |

*Primary Examiner*—Robert A. Dawson
*Assistant Examiner*—W. L. Millard

[57] ABSTRACT

An improvement in an apparatus for separating fluids or non-biotechnological products in solution, wherein said apparatus has a fibrous element which permits flow of fluids therethrough and is composed of irreversibly set non-graphitic carbonaceous fibers having an LOI greater than 40.

10 Claims, 1 Drawing Sheet

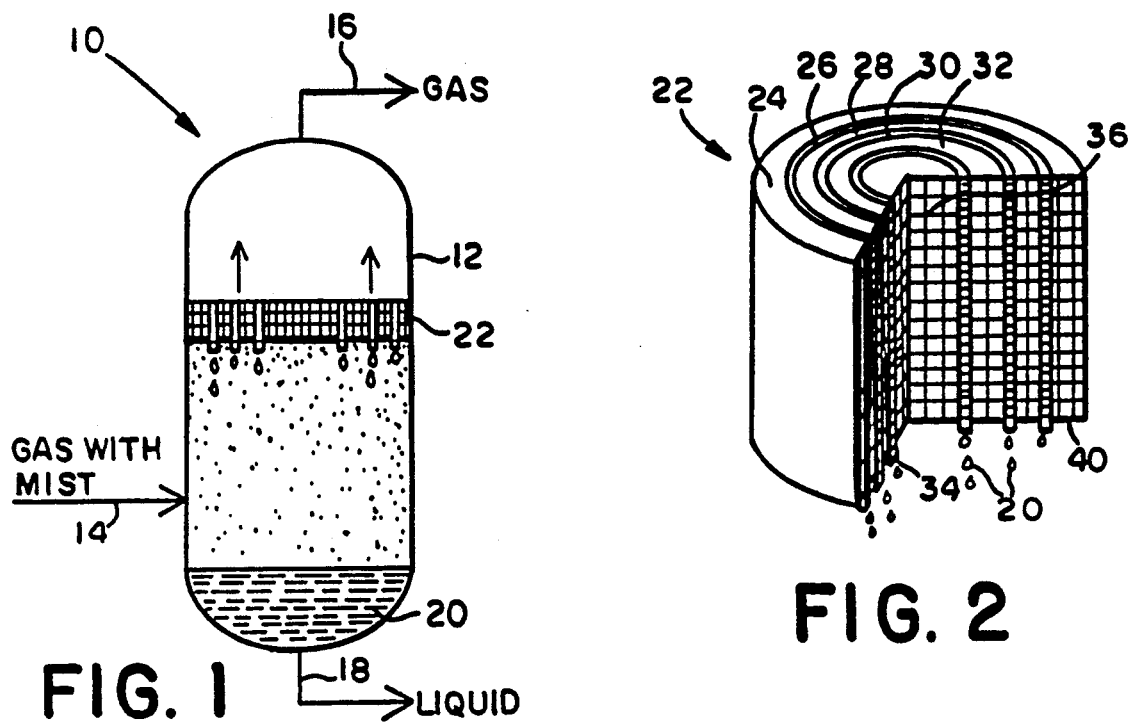
FIG. 1
FIG. 2
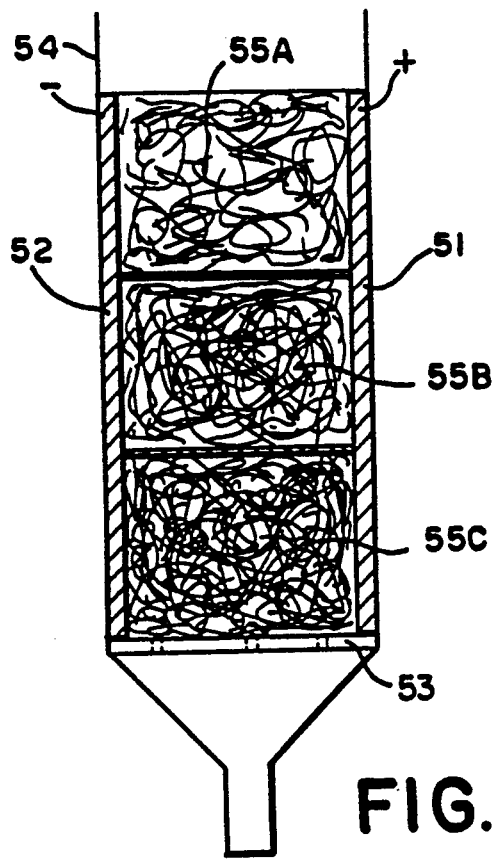
FIG. 3

METHOD FOR SEPARATING FLUIDS USING A CARBONACEOUS POLYMERIC FILTER HAVING A LOI GREATER THAN 40

This is a divisional application of Ser. No. 581,339, filed Sep. 11, 1990, which is now U.S. Pat. No. 5,151,198.

FIELD OF THE INVENTION

The present invention relates to a novel fibrous element for use in separators for non-biotechnological products. More particularly, there is provided structures comprising non-graphitic carbonaceous fibers which are utilized in fluid separating devices or devices such as demisters, column separators, filtration apparatuses, electrophoresis apparatuses, and the like.

BACKGROUND OF THE INVENTION

Fibrous elements that work effectively in demisting, column packing and filtration applications ideally should possess at least some of the characteristics of being inert in the system of use, have a high temperature stability, a low pressure drop, not wetted and/or swollen by the fluid system in use, have good flame arresting properties in the presence of flammable fluids, have sufficient conductivity to render anti-static or grounding properties, can be used with an electrical field or gradient electrical field to enhance separation and have good vibration stability without vitrification with time at temperature. No single material or combination of materials prior to the present invention is capable of being customized to contain a desired combination of these properties.

Mist eliminator mesh pads are typically pads composed of elements, such as knitted wire mesh, and are commonly placed in a gas-liquid contact apparatus to remove mist from a mist-containing gas stream. Typically, such mist eliminator mesh pads are composed of fibrous or filament elements, such as four to fifteen mil diameter stainless steel wire. These elements are arranged from about three to twenty-four inches in thickness, have a density ranging from about four to fifteen pounds per cubic foot and range in diameter from about one to thirty feet depending upon the gas-liquid contact apparatus in which the pads are employed. Such mist eliminator mesh pads are generally effective in removing droplets as small as one to five micrometers from mist containing gas streams.

Metallic filaments cannot be utilized in many corrosive atmospheres, for example, those containing non-oxidizing acids or where electrical conductivities may present a hazard.

The capacity of a mist eliminator mesh pad in a gas-liquid contact apparatus, i.e. the maximum gas velocity of the gas stream through the mesh pad, is generally limited by the mesh pad's ability to drain rapidly the coalesced liquid collected by the mesh pad. One attempt to increase the capacity of mist eliminator mesh pads and to reduce the mesh pad's pressure drop has been the employment of drainage cylinders or ancillary rolls of wire mesh fixed to the bottom of conventional mist eliminator mesh pads. Such a drainage cylinder of ancillary rolls is provided for localized, separate regions of flow interruption and interception, thereby creating a preferential drainage foci. (See, for example, U.S. Pat. No. 4,022,593, issued May 10, 1977, hereby incorporated by reference in its entirety.)

In some limited cases, it has been the past practice to employ variable high and low density mesh pads in a vapor phase intercept pattern to enhance mist elimination performance. In such cases, the lower portion of the mesh pad is formed of a low density material to promote rapid and easy draining of coalesced liquid and to aid in working away precipitated material from the pad. The upper portion of the pad is formed of a high density material to collect liquid particulates from the upwardly flowing, mist containing vapor stream.

It is desirable to provide an improved mist eliminator mesh pad in order to improve the mesh pad's capacity and to provide for reductions in pressure drop compared to conventional mesh pads.

There have been many recent advances in the use of pulsed field electrophoresis and the separation of molecules based on their migration through an electrical field. Electrophoresis separation is generally accomplished by establishing an electrical field between two electrodes in a gel such as an argose gel. Column separation of molecules has been accomplished using electrically conductive polymers such as polyethylene oxides or polypyrrole copolymers. However, such polymers and gels have only found limited application and cannot be utilized in many common solvent systems. Also, the prior conductive polymers do not provide a sufficient variant in pulsed fields to perform many simple separations.

There is a need to provide a means for separating molecules in solution, for example, removal of by-products in chemical reactions, desalination, removal of solvents, and the like.

U.S. Pat. No. 4,837,076 to Mc Cullough et al, which is herewith incorporated by reference discloses a class of carbonaceous fibers which can be used in the present invention.

U.S. Pat. No. 4,744,806 to Ozolins et al, which is herewith incorporated by reference, discloses demister pads and apparatus which are similar to the apparatuses and pads of the invention except that the pads are metallic and cannot be used with an electrical field for separation.

The carbonaceous fibers of the invention according to the test method of ASTM D 2863-77 have an LOI value greater than 40. The test method is also known as "oxygen index" or "limited oxygen index" (LOI). With this procedure the concentration of oxygen in $O_2/N_2$ mixtures is determined at which a vertically mounted specimen is ignited at its upper end and just continues to burn. The size of the specimen is $0.65 \times 0.3$ cm with a length from 7 to 15 cm. The LOI value is calculated according to the equation:

$$LOI = \frac{[O_2]}{[O_2 + N_2]} \times 100$$

The LOI values of different materials are as follows:

| | |
|---|---|
| polypropylene | 17.4 |
| polyethylene | 17.4 |
| polystyrene | 18.1 |
| rayon | 18.6 |
| cotton | 20.1 |
| nylon | 20.0 |
| polycarbonate | 22 |
| rigid polyvinyl chloride | 40 |
| stabilized polyacrylonitrile | >40 |

| | |
|---|---|
| -continued | |
| graphite | 55 |

The term "non-graphitic" as used herein relates to those carbonaceous fibers having an elemental carbon content of less than 92 percent (%), are substantially free of oriented carbon or graphite microcrystals, and as further defined in U.S. Pat. No. 4,005,183, which is herein incorporated by reference.

The term "carbonaceous fibers" refers to fibers having a carbon content of at least 65%, which carbon content has been increased after an irreversible chemical change such as brought about by heat treatment as disclosed in U.S. Pat. No. 4,837,076.

It should be understood that the reversible fiber deflection of the non-linear carbonaceous fiber comprises two components, pseudoelongation and fiber elongation. Pseudoelongation results from the non-linear configuration and/or false twist imposed on the fiber. Fiber elongation is the elongation to fiber break after the fiber has been made linear.

SUMMARY OF THE INVENTION

According to the present invention there is provided an improved fibrous element for apparatuses having a fibrous element which is used for separating fluids or non-biotechnological products in solution. The improved fibrous element of the invention comprises non-flammable irreversibly set non-graphitic carbonaceous polymeric fibers having an LOI greater than 40. The fibers may be in the form of a batting, matting, webbing or felt, a woven or non-woven fabric, knitted cloth or the like, depending upon the particular apparatus in which they are utilized.

The fibrous elements of the invention are capable of being used in non-oxidizing acidic environments or in bases where aluminum filters would corrode.

The carbonaceous fibers have a carbon content of at least 65% and an aspect ratio (length/diameter; l/d) of greater than 10:1. The fibers may be linear, non-linear or a combination of linear and non-linear fibers. The non-linear fibers are resilient, shape reforming and have a reversible deflection greater than about 1.2:1.

The fibrous elements comprising the carbonaceous fiber of the invention may be separators for gas-liquid, gas-gas, or liquid-liquid systems and solutions containing large molecules.

What is meant by biotechnological products are natural products including those prepared by genetic engineering such as RNA and DNA, microorganisms, yeasts, and the like. It should also be understood that the term "large molecules" is intended to mean non-biotechnological products of the type that are capable of separation by pulsed field electrophoresis.

The fibrous element can comprise regions of high density and low density areas for separation of liquids from a gas stream and for the separation of molecules using electrophoresis type of separation techniques. The different density areas can be achieved by varying the fiber diameters, using carbonaceous fibers of different heat treatment, using fabrics of different weaves, etc.

The fibrous element can comprise layers of carbonaceous fibers having different electrical conductivities. This type of arrangement is particularly suitable for the separation of large molecules having different molecular weights and electrical charges where the separation is the result of an induced electrical field.

The invention will be described for the purposes of illustration only in connection with certain embodiments; however, it is recognized that various changes, modifications, additions and improvements may be made in the illustrated embodiment by those persons skilled in the art without departing from the spirit and scope of the invention.

BRIEF DESCRIPTION OF THE DRAWINGS

FIG. 1 is an illustrative sectional view of a gas-liquid mist eliminating contact tower containing a layer of the carbonaceous fiber as the fibrous element;

FIG. 2 is an enlarged perspective partial sectional view of the mist eliminator of FIG. 1, and, FIG. 3 is an illustrative sectional view of a separation tower with different layers of carbonaceous fibers.

DESCRIPTION OF THE EMBODIMENTS

FIG. 1 shows a gas-liquid contacting system 10 which comprises a gas-liquid contact tower 12 having an inlet 14 at the lower portion thereof for the introduction of a mist-laden gas stream in which the mist particles are to be removed. There is provided an upper portion 16 for the removal of coalesced liquid 20 from the gas-liquid tower 12. Across the diameter of the tower 12 is shown a variegated density, mist eliminator pad 22 of carbonaceous fibers. The pad 22 is placed in the gas flow path of the mist-containing gas stream. The pad 22 comprises a cylindrical, spiral-wound mesh, wound to the dimensions of the gas-liquid contact tower 12.

FIG. 2 is an enlarged view of the pad 22 showing high density layers 26, 30 and 34 providing a plurality of spiral-wound, higher density regions, preferably, two to six, and layers 24, 28, 32 and 36 providing a plurality of low-density regions, preferably two to six. The high density regions provide for the coalescing and drainage of coalesced liquid 20. As illustrated, the high density region may extend slightly downward from the upstream face 40 of the mesh pad to promote more rapid drainage from the mesh pad 22.

FIG. 3 illustrates a separation column 50 in its simplest form. The separation column 50 is composed of a tower 54 having an apertured disk 53 near its bottom and a pair of electrodes 51, 52 along the sides which provide an electrical charge. Within the column 50 there is placed layers 55A, 55B, 55C of carbonaceous fibers of different electrical conductivities and/or densities. The electrodes 51, 52 create an electrical field through the carbonaceous fibers which affect the migration of different molecules through the column. Suitably, the column is used with a programmable power supply having 100 to 500 V or 100 to 1000 mA capabilities.

The separation column can be used in purification procedures for a large group of non-biotechnological chemical compounds capable of pulsed field separation including the removal of by-products of chemical reactions, removal of impurities from liquids, desalination, and the like.

The carbonaceous fibers used in the invention are prepared, as disclosed in U.S. Pat. No. 4,837,076, by heat treating a suitable stabilized carbonaceous precursor material which can be made into carbonaceous fibers or filaments and which are thermally stable. A suitable precursor material may be, for example, derived from a stabilized polymeric material or stabilized pitch (petroleum or coal tar) based materials. Preferably, the precursor material used in the present invention is derived from stabilized acrylic based filaments such as stabilized polyacrylonitrile based fibers.

The polyacrylonitrile fibers which are advantageously utilized in preparing the carbonaceous fibers are selected from acrylonitrile homopolymers, acrylonitrile copolymers and acrylonitrile terpolymers. The copolymers preferably contain at least about 85 mole percent of acrylonitrile units and up to 15 mole percent of one or more monovinyl units, e.g. styrene, methylacrylate, methyl methacrylate, vinyl chloride, vinylidene chloride, vinyl pyridine, and the like, copolymerized therewith. Also, the polyacrylonitrile based fibers can comprise terpolymers, preferably, wherein the acrylonitrile units are at least about 85 mole percent.

The density of the material can be controlled by the degree of entanglement to produce anywhere from low density, high loft material used for the mesh pad to a high density material that is able to produce significant pressure drops of gases flowing through the pad.

The carbonaceous fibers derived from polyacrylonitrile based materials which can be utilized in the invention are classified into three groups.

In a first group, the carbonaceous fibers have a carbon content of greater than 65 percent but less than 85 percent, are electrically nonconductive, and do not possess any electrostatic dissipating characteristics, i.e., they are not able to dissipate an electrostatic charge. Such fibers are useful where electrical charges or static electricity should be avoided.

The term electrically nonconductive as utilized in the present invention relates to a resistance of greater than $4 \times 10^6$ ohms/cm ($10^7$ ohms/in) when measured on a 6K (6000 filaments) tow of individual fibers having a diameter of from 4 to 20 microns.

When linear carbonaceous fibers are being utilized in the invention it is preferable that the fibers having the electrical characteristics of the first group. The preferred linear fibers also have a fiber elongation of about 3 to 9 percent and a tenacity of about 2 to 6 grams/denier (g/d).

When the fiber is a stabilized and heat set polyacrylonitrile based fiber it has been found that a nitrogen content of 18 percent or higher results in an electrically nonconductive fiber.

In a second group, the carbonaceous fibers are classified as being partially electrically conductive (i.e., having a low conductivity) and having a carbon content of greater than 65 percent but less than 85 percent. Low conductivity means that a 6K tow of fibers in which the individual precursor fibers have a diameter of from 4 to 20 micrometer, has a resistance when measured on a 6K tow of from $4 \times 10^6$ to $4 \times 10^3$ ohms/cm ($10^7$–$10^4$ ohms/in.).

When linear fibers of this group are utilized in the invention, it is preferable that the fibers also have a fiber elongation of about 3 to 6 percent and a tenacity of from about 3 to 7 g/d.

In a third group are the fibers having a carbon content of at least 85 percent but less than 98%, preferably, less than 92%. These fibers are characterized as having a high electroconductivity. That is, the fibers have an electrical resistance when measured on a 6K tow of less than $4 \times 10^3$ ohms/cm ($10^4$ ohms/in).

When linear fibers having the electrical characteristics of the third group are utilized, it is preferable that such fibers also have an elongation of about 2 to 4% and a tenacity of about 4 to 9 g/d.

The carbonaceous fibers employed in the present invention can be used in substantially any desired fabricated form depending on the purpose for which the structure in which they are incorporated is to be used.

In one embodiment, the fiber assembly can be the original irreversibly heat set knitted fabric containing the carbonaceous fibers.

In another embodiment of this invention, the assembly can include the individual carbonaceous fibers in a densified batting of long or short fibers. The carbonaceous fibers generally can be from 3 mm to 12.5 cm in length.

In still another embodiment, the assembly can be carbonaceous fibers used in the form of a yarn or tow composed of many filaments.

In still another embodiment the assembly can be the carbonaceous fibers which have been stretch broken, formed into spun yarn and then fabricated into a knitted cloth, for example, plain jersey knit, interlock, ribbed, cross float jersey knit or weft knit and the like, or woven into a fabric, for example of plain weave, satin weave, twill weave, basket weave, and the like. The woven fabric can combine the nonlinear carbonaceous fibers, for example, as warp.

The fiber assembly can also be in the form of a nonwoven material or fabric such as a web, mat, fluff or batting of fibers such as described above. In another embodiment the assembly can include the wool-like fluffy material produced from the thermally set knitted fabric which contains the nonlinear fibers. The assembly in the form of a batting or wool-like fluff can be processed by conventional needle-punching means.

A densified mat or batting can be prepared by the procedure described in copending patent application Ser. No. 344,327 of Mc Cullough et al, filed Apr. 27, 1989, entitled "Lock Set Structures", which is herein incorporated by reference. Accordingly, a densified structure is provided by interlocking the permanently set carbonaceous fibers with similar precursor fibers and heat setting the entire structure. The resulting densified structure then contains carbonaceous fibers of similar electroconductivities throughout.

Also, there is provided a means for interlocking two mats or battings of different carbonaceous fibers so as to form a filter element with varied densities or conductivities.

What is claimed is:

1. A method for separating fluids in a column comprising passing a fluid for separation through a column having a fibrous element comprising non-graphitic carbonaceous fibers derived from oxidized polyacrylonitrile fibers having an electrical conductivity and an LOI greater than 40 and a carbon content of at least 65% which is the result of an irreversible chemical change whereby an increase of carbon content has occurred, passing an electrical current through said fibrous element so as to affect migration and separation of the fluids through the column, and collecting the liquid separated.

2. The method of claim 1, wherein said fibrous element comprises layers of carbonaceous fibers having different electrical conductivity.

3. The method of claim 1, wherein said fibrous element comprises layers of carbonaceous fibers providing different density regions.

4. The method of claim 1, wherein said fibrous element is comprised of high and low density regions and layers of carbonaceous fibers having different electrical conductivities.

5. The method of claim 1 wherein said carbonaceous fibers are non-linear, have a reversible deflection ratio of greater than 1.2:1 and an aspect ratio greater than 10:1.

6. The method of claim 1 wherein a mist-containing gas steam is passed across said carbonaceous fibers.

7. The method of claim 1 which is a desalination process.

8. The method of claim 1 wherein said carbonaceous fibers are derived from stabilized polyacrylonitrile based fibers.

9. The method of claim 1 wherein said fluid comprises non-biotechnical products.

10. The method of claim 1 wherein solids are separated from said fluid.

* * * * *